United States Patent
Wiesbeck

(10) Patent No.: US 9,073,889 B2
(45) Date of Patent: Jul. 7, 2015

(54) PROCESS FOR THE MANUFACTURE OF TAXIFOLIN FROM WOOD

(75) Inventor: Franz Wiesbeck, Feusisberg (CH)

(73) Assignee: LDA AG, Wollerau (CH)

( * ) Notice: Subject to any disclaimer, the term of this patent is extended or adjusted under 35 U.S.C. 154(b) by 0 days.

(21) Appl. No.: 14/376,397

(22) PCT Filed: Feb. 2, 2012

(86) PCT No.: PCT/EP2012/000474
§ 371 (c)(1),
(2), (4) Date: Nov. 20, 2014

(87) PCT Pub. No.: WO2013/113329
PCT Pub. Date: Aug. 8, 2013

(65) Prior Publication Data
US 2015/0080587 A1   Mar. 19, 2015

(51) Int. Cl.
*C07D 311/30* (2006.01)
*C07D 311/62* (2006.01)

(52) U.S. Cl.
CPC .................................... *C07D 311/62* (2013.01)

(58) Field of Classification Search
CPC ...................................................... C07D 311/30
See application file for complete search history.

(56) References Cited

FOREIGN PATENT DOCUMENTS

| | | |
|---|---|---|
| EP | 2143435 A1 | 1/2010 |
| WO | 2011/155829 A1 | 12/2011 |

OTHER PUBLICATIONS

International Search Report and Written Opinion dated Nov. 15, 2012 for Application No. PCT/EP2012/000474.

*Primary Examiner* — Sun Jae Yoo
(74) *Attorney, Agent, or Firm* — Patterson & Sheridan, L.L.P.

(57) ABSTRACT

The invention relates to a process for the manufacture of taxifolin, comprising the following steps: stacking the wood particles in a percolator, extracting the wood particles in the percolator using ethanol to dissolve at least resins, oils, and taxifolin, discharging the ethanolic extract from the percolator, and purifying the ethanolic extract for the manufacture of taxifolin with the following steps in the specified order: preparing a mixture of water and the ethanolic extract, mixing the mixture at between 70° C. and 99° C. so that taxifolin in the aqueous phase of the mixture goes into the solution, cooling the mixture to below 65° C. for separating and removing the resin phase and the oil phase from the water phase, adding taxifolin seed crystals to the water phase, temperature controlling the water phase at between 0° C. and 30° C. for the crystallization of taxifolin, and separating the crystallized taxifolin from the mother liquor.

13 Claims, 2 Drawing Sheets

PROCESS FOR THE MANUFACTURE OF TAXIFOLIN FROM WOOD

Figure 1:
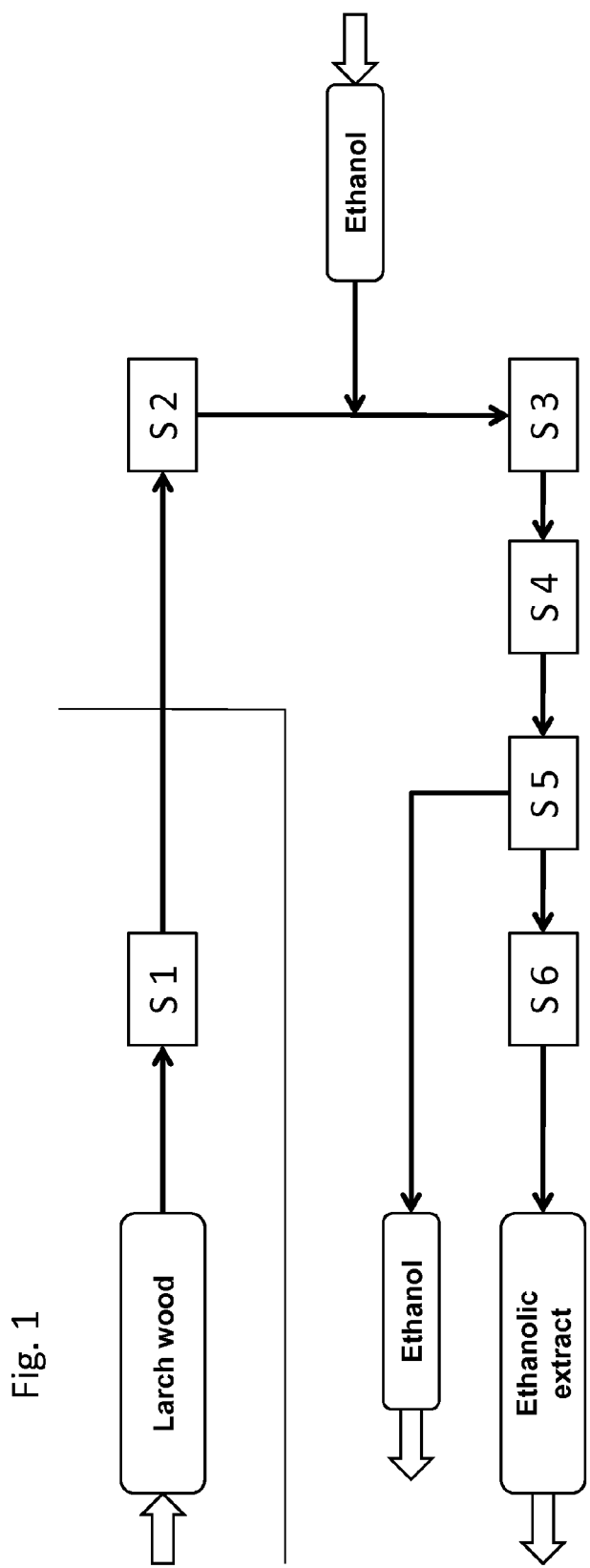

This invention relates to a process for the manufacture and/or isolation of taxifolin from wood, particularly from larch wood.

The state of the art knows different processes for the manufacture of taxifolin (also: dihydroquercetin) from larch wood. However, the state of the art processes show only processes for manufacturing small amounts, particularly for the pharmaceutical industry. These methods are not suitable for an economically viable manufacture of large quantities of this valuable material.

It is the object of the present invention to provide a process which, with cost-effective and environmentally sound implementation, allows for the economical manufacture of the purest strain possible of taxifolin from wood.

The problem is solved by the features of claim 1. The object of dependent claims is the preferred embodiments according to the invention.

Thus, the object is achieved by a process for the manufacture of taxifolin. The process comprises the following steps in the given order: First, wood particles are stacked in a percolator. Larch wood is preferred. Of particular preference for use are wood particles from the lower trunk and/or of the root stock of the larch, particularly the Siberian larch (*larix sibirica/larix dahurica*). The reason for this is the high content of taxifolin in the trunk portion and/or the rootstock of larch. In particular, wood bark, sapwood and branches are removed and not used for extraction. After the wood particles have been stacked in the percolator, the extraction from the wood particles is carried out using ethanol to dissolve resins and oils and therefore also taxifolin. After extraction has been carried out, the ethanolic extract is discharged from the percolator. The ethanolic extract is then purified in order for taxifolin to be manufactured in the following steps and order: (i) forming a mixture of water and the ethanol extract; preferably, at least the water is admixed at an amount that is equal to the ethanolic extract, (ii) mixing the mixture between 70° C. and 99° C., so that taxifolin goes in the aqueous phase of the mixture into solution; in particular, it is in this temperature range that taxifolin goes into solution from the resin into the water, (iii) cooling the mixture to below 65° C. for separating and removing the resin phase and the oil phase from the water phase, (iv) adding taxifolin seed crystals to the water phase, (v) maintaining the water phase temperature between 0° C. and 30° C. for the crystallisation of the taxifolin, and (vi) separating the crystallised taxifolin from the mother liquor.

Preferably ethanol is used for extraction at a concentration of at least 70%, preferably at least 80%, more preferably at least 95%. The residual extract is preferably dissolved by applying a vacuum/low-pressure to the percolator and a final flushing of the wood particles in the percolator using fresh ethanol and a subsequent mixing of the ethanolic extract.

Prior to purification, the ethanolic extract is concentrated by evaporation, preferably to a concentration between 50 and 250 g/L (grams per liter) taxifolin. The temperature and pressure conditions for the evaporation are chosen such that the content of ethanol is reduced in the ethanolic extract. Preferably, the evaporation is carried out at a temperature between 55° C. and 70° C. and reduced pressure.

The subsequent purification process has the following preferred steps:

Preparing the mixture of water and ethanolic extract, preferably at a temperature between 70° C. and 95° C. This mixture is thus well preheated for mixing. Directly before and/or when mixing the mixture, a reduction of the ethanol content in the mixture occurs preferably by evaporation.

Advantageously, the mixture is actively mixed, preferably by means of a stirrer. For an optimum dissolving of the taxifolin in the aqueous phase, a temperature range for mixing between 70° C. and 99° C. has proven to be advantageous, preferably between 70° C. and 95° C., more preferably between 80° C. and 95° C. Immediately before and/or when mixing the mixture it is preferable if more water is added to the mixture. In particular, at least the same amount of water is added as mixture still present after evaporation of the mixture.

After mixing, the separation of the resin phase (bottom phase) from the water phase (upper phase) and the oil phase (top phase) occurs by cooling the mixture to below 65° C. Preferably, the mixture is cooled for at least 30 minutes from 70° C. to 99° C. (mixing temperature) at 35° C. to 64° C. After cooling, the resin phase is separated from the mixture and preferably the resin phase is returned to the mixture at least once prior to cooling. Preferably, the resin phase is returned to the mixture before and/or during the aforementioned mixing. After the resins have been returned at least once, the resin phase is discharged and the oil phase is separated and removed from the water phase.

In the next step, the taxifolin seed crystals are added to the water phase, and the crystallisation of taxifolin is carried out by cooling. This is followed by the separation of the crystallised taxifolin from the mother liquor and removal of said mother liquor.

Preferably, at least one re-crystallisation with the following steps then occurs in the given order: dissolving the crystallised taxifolin that has been separated from the mother liquor in water at between 70° C. and 99° C., adding taxifolin seed crystals, controlling the temperature of the water at between 0° C. to 30° C. for the crystallisation of taxifolin, separating the re-crystallised taxifolin from the mother liquor, and then removing the mother liquor.

It is preferably provided that during the first and/or re-crystallisation, the addition of taxifolin seed crystals occurs when a first temperature of the water is between 30° C. and 65° C., preferably between 45° C. and 60° C., and the water is temperature-controlled to crystallise out at a second temperature between 0° C. and 30° C., preferably between 20° C. and 10° C. Cooling from the first temperature to the second temperature occurs preferably for between 5 and 15 hours. It is particularly advantageous for the crystallisation to maintain the second temperature for between 0.5 and 2 hours.

After crystallisation, the crystallised taxifolin is washed with cold water (below 50° C.), and the washed taxifolin is then dried.

Throughout the described process, during the extraction and purification, it is preferable to use only water and ethanol. Preferably, neither the wood nor the extract nor taxifolin is treated with substances other than water or ethanol. For the mixture and the crystallisation, only water without any additives is preferably used so as to avoid any contamination of the taxifolin.

An embodiment of the process according to the invention is explained with reference to the accompanying drawing. Shown in the drawings:

FIG. 1 an extraction sequence of the process according to the invention, and

Figure 2:
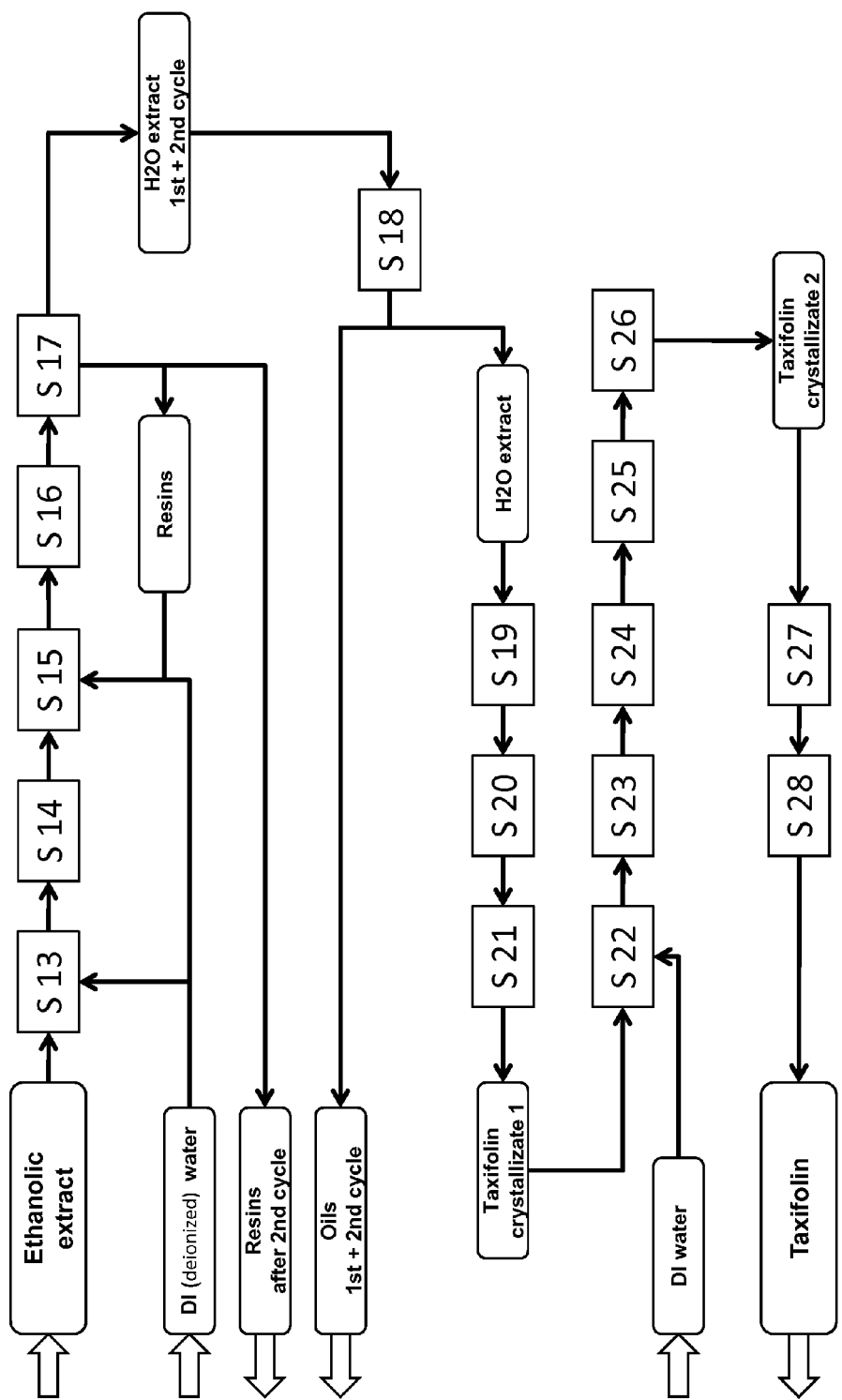

FIG. 2 a taxifolin purification sequence of the process according to the invention.

FIG. 1 shows the steps S1 to S6 for the extraction from larch wood. After step S6, steps S13 to S28 follow in accordance with FIG. 2 for the purification of the taxifolin.

The starting material is the lower trunk portion of the larch, particularly the Siberian larch (*larix sibirica*), in particular the dahuric larch (*larix dahurica*), particularly *larix* spp. is used. Comminution of wood takes place in step S1. This is achieved particularly by means of a chopper and/or a hammer mill. In step S2, the comminuted wood particles are stacked in a percolator. In step S3, ethanol is introduced into the percolator. In particular, the ethanol is introduced at the top of the percolator and collected at the bottom. Using a pump, the ethanol is repeatedly pumped through the percolator. In step S4, the obtained ethanolic extract is discharged from the percolator and evaporation of the ethanol extract occurs in step S5. A portion of the ethanol is evaporated. In step S6, the concentrated ethanolic extract is transferred to step S13 (see FIG. 2).

At the start of the purification of the ethanolic extract to obtain taxifolin, the solvent is changed. In step S13, the ethanolic extract is mixed with water and re-evaporation takes place in step S14. The temperature and pressure conditions in step S14 are selected such that ethanol is predominantly evaporated. In step S15, water is added again and active mixing, preferably with a stirrer, is conducted so that the taxifolin goes into solution from the resins into the water. This is also known as an aqueous resin extraction or a liquid/liquid extraction in step S15. The mixing in step S15 is preferably performed at the same or higher temperature than the evaporation in S14.

In step S16, the mixture from S15 is cooled. In particular, cooling takes place for a long period so that the resin phase settles in the mixture. This cooling enables the mixture to separate into a resin phase (lower phase) and a liquid phase (upper phase). In this upper phase, oils are located at the very top and an aqueous phase is located between the resin phase and the oils. In step S17, the oils and the aqueous phase are separated from the resin. The resin is again returned to step S15. This return of the resins is carried out at least once. After the second cycle, the resins are removed. The upper phase consisting of oils and aqueous phase of the two cycles is separated in step S18. The oils are then removed. The remaining aqueous extract is further processed by crystallisation and washing processes in following steps.

In step S19, taxifolin seed crystals are added to the aqueous phase. In step S20, cooling occurs slowly, so that the taxifolin is crystallised. The mother liquor is removed in step S21 and the crystallised taxifolin is again mixed with water in step S22. Here, a higher temperature is chosen so that the taxifolin again dissolves in the water. Cooling occurs in step S23 and the taxifolin seed crystals are added in step S24. In step S25, further cooling occurs slowly so that the taxifolin is crystallised. In step S26, again the mother liquor is discharged and the crystallised taxifolin can be washed in step S27. Washing is carried out by adding cold water. This is followed by drying in step S28, preferably using inert gas. After drying, a taxifolin content of 85-95% is obtained.

The taxifolin content of the final product was determined based on the known molecular weight of taxifolin and the peak area of the established liquid chromatographic analysis process (HPLC/UPLC). The determined taxifolin contents here were between 90 and 92%. The purity of the samples was also determined by means of the liquid chromatographic analysis process over the peak area ratio (% area) of the sample chromatogram and averaged between 82 and 83% of the area. The main impurities consist of 6% area dihydrokaempferol, 7% area quercetin, 0.8% area naringenin and 0.6% area epitaxifolin.

The invention claimed is:

1. A process for the manufacture of taxifolin, comprising: stacking wood particles in a percolator, extracting the wood particles in the percolator with ethanol to dissolve at least resins, oils, and taxifolin, discharging the ethanolic extract from the percolator, and purifying the ethanolic extract for the manufacture of taxifolin, the purifying sequentially comprising:
   producing a mixture of water and the ethanolic extract, mixing the mixture at between 70° C. and 99° C., so that taxifolin in the aqueous phase of the mixture goes into the solution,
   cooling the mixture to below 65° C. for separating and removing the resin phase and the oil phase from the water phase,
   adding taxifolin seed crystals to the water phase,
   temperature controlling the water phase at between 0° C. and 30° C. for the crystallisation of taxifolin, and
   separating the crystallised taxifolin from the mother liquor.

2. The process according to claim 1, characterised by concentrating the ethanolic extract by means of evaporation prior to purification.

3. The process according to claim 1, characterised in that ethanol with a concentration of at least 70% is used for the extraction.

4. The process according to claim 1, characterised in that the mixture is produced at a temperature between 70° C. and 95° C.

5. The process according to claim 1, characterised by a reduction of the ethanol content in the mixture by evaporation immediately before or while preparing the mixture.

6. The process according to claim 1, characterised in that the mixture is mixed actively by means of a stirrer.

7. The process according to claim 1, characterised in that directly before or when mixing the mixture, extra water is added to the mixture.

8. The process according to claim 1, characterised in that the mixture is mixed at 80° C. to 95° C.

9. The process according to claim 1, characterised by at least one return of the separated resin phase to the mixture before or when mixing.

10. The process according to claim 1, characterised by at least one re-crystallisation with the following steps in the specified order: dissolving the crystallised taxifolin separated from the mother liquor in water at between 70° C. and 99° C., adding taxifolin seed crystals to the water, temperature controlling the water at between 0° C. and 30° C. for the crystallisation of the taxifolin, separating the re-crystallised taxifolin from the mother liquor, and removing the mother liquor.

11. The process according to claim 1, characterised in that during the first and/or re-crystallisation, the taxifolin seed crystals are added at a first temperature of the water between 30° C. and 65° C., and for crystallisation the water is temperature controlled at a second temperature between 0° C. and 30° C.

12. The process in claim 11, characterised in that the cooling from the first temperature to the second temperature takes place for between 5 and 15 hours.

13. The process according to claim 1, characterised by washing the crystallised taxifolin with water below 50° C. and drying the washed taxifolin.

* * * * *